United States Patent
Varga et al.

(10) Patent No.: US 11,083,956 B1
(45) Date of Patent: Aug. 10, 2021

(54) CUSTOMIZABLE GUARD

(71) Applicant: Dental Choice Holdings LLC, Louisville, KY (US)

(72) Inventors: Andrew M. Varga, Louisville, KY (US); Manese Rabeony, Piscataway, NJ (US); Monroe Elkin, Lake Worth, FL (US)

(73) Assignee: Dental Choice Holdings LLC, Louisville, KY (US)

( * ) Notice: Subject to any disclaimer, the term of this patent is extended or adjusted under 35 U.S.C. 154(b) by 0 days.

(21) Appl. No.: 16/420,920

(22) Filed: May 23, 2019

Related U.S. Application Data

(60) Provisional application No. 62/676,581, filed on May 25, 2018.

(51) Int. Cl.
| | | |
|---|---|---|
| A63B 71/12 | (2006.01) | |
| A63B 71/10 | (2006.01) | |
| A61F 5/01 | (2006.01) | |
| A63B 71/14 | (2006.01) | |

(Continued)

(52) U.S. Cl.
CPC ........ *A63B 71/1225* (2013.01); *A61F 5/0104* (2013.01); *A63B 71/08* (2013.01); *A63B 71/10* (2013.01); *A63B 71/1291* (2013.01); *A63B 71/14* (2013.01); *A63B 2071/0063* (2013.01); *A63B 2071/125* (2013.01); *A63B 2071/1283* (2013.01)

(58) Field of Classification Search
None
See application file for complete search history.

(56) References Cited

U.S. PATENT DOCUMENTS

| | | | |
|---|---|---|---|
| 2,659,366 | A | 11/1953 | Savarese |
| 5,052,409 | A | 10/1991 | Tepper |
| 5,405,312 | A | 4/1995 | Jacobs |

(Continued)

FOREIGN PATENT DOCUMENTS

| | | |
|---|---|---|
| CA | 2668913 A1 | 5/2008 |
| GB | 2513902 A | 11/2014 |

(Continued)

OTHER PUBLICATIONS

U.S. Appl. No. 62/676,581 entitled "Customizable Protective Equipment for Athletics" filed May 25, 2018.

(Continued)

*Primary Examiner* — Chinessa T. Golden
(74) *Attorney, Agent, or Firm* — Middleton Reutlinger

(57) ABSTRACT

A moldable portion for use with protective equipment, guards, braces, or the like for use to protect from injury and facilitate healing of the same are disclosed herein. This moldable portion includes a thermoplastic semi-crystalline propylene ethylene copolymer having a crystallinity of about 2% to about 65% that is between about 85% to about 99% of the moldable portion and a microwave susceptor that is about 1% to about 15% of the moldable portion These moldable portions may be adapted to be positioned adjacent an area of an user's anatomy it is intended to protect, and may be prepared for customization by heating to a temperature of about 60° C. to about 100° C. and shaped and configured to be affixed to a portion of the protective equipment.

20 Claims, 14 Drawing Sheets

(51) Int. Cl.
    *A63B 71/08*    (2006.01)
    *A63B 71/00*    (2006.01)

(56) References Cited

U.S. PATENT DOCUMENTS

| | | |
|---|---|---|
| 7,798,149 B2 | 9/2010 | Haduong |
| 7,890,193 B2 | 2/2011 | Tingey |
| 7,950,394 B2 | 5/2011 | Elkin et al. |
| D641,478 S | 7/2011 | Belvedere et al. |
| 8,667,972 B2 | 3/2014 | Makkar et al. |
| 8,689,797 B2 | 4/2014 | Elkin et al. |
| 8,951,217 B2 | 2/2015 | Joseph |
| 9,668,827 B2 | 6/2017 | Roettger et al. |
| 9,968,419 B2 | 5/2018 | Alvarez et al. |
| 10,328,225 B2 | 6/2019 | Gamer |
| 2002/0144695 A1 | 10/2002 | Cook |
| 2004/0094165 A1 | 5/2004 | Cook |
| 2007/0289600 A1 | 12/2007 | Li |
| 2008/0099029 A1 | 5/2008 | Lamberg |
| 2012/0196061 A1* | 8/2012 | Weisinger ............... B32B 27/08 428/35.2 |
| 2013/0042876 A1 | 2/2013 | Hermanson |
| 2013/0303680 A1* | 11/2013 | Weaver ................... C08L 23/16 524/528 |
| 2014/0272379 A1* | 9/2014 | Watkins ............... A43B 13/125 428/316.6 |
| 2015/0010765 A1* | 1/2015 | Munro ................... C08L 53/00 428/516 |
| 2017/0020716 A1 | 1/2017 | Hart et al. |
| 2018/0207022 A1 | 7/2018 | Alvarez |
| 2019/0262565 A1 | 8/2019 | Gamer |
| 2019/0374734 A1 | 12/2019 | Gamer |

FOREIGN PATENT DOCUMENTS

| | | |
|---|---|---|
| JP | 2006519656 A | 8/2006 |
| JP | 5008394 B2 | 8/2012 |
| JP | WO2014188517 A | 2/2017 |

OTHER PUBLICATIONS

U.S. Appl. No. 16/516,958 entitled "Single Arch Dental Device and Method of Manufacture" filed Jul. 19, 2019.
exxonmobilchemical.com, Product Datasheet for Vistamaxx(TM) 3980FL Performance Polymer, 2 pages, Jul. 14, 2020.
exxonmobilchemical.com, Product Datasheet for Vistamaxx(TM) 6102FL Performance Polymer, 2 pages, Jul. 14, 2020.
exxonmobilchemical.com, Product Datasheet for Vistamaxx(TM) 3000 Performance Polymer, 2 pages, Jan. 1, 2017.

* cited by examiner

CUSTOMIZABLE GUARD

BACKGROUND

Various pieces of protective equipment or guards are often worn by athletes during sporting events to protect the athletes from injury. Various guards, braces, or the like are also often worn following an injury to protect the injured area and promote healing. Such protective equipment, guards, or the like are often constructed of synthetic materials, for example foam rubbers, elastics, and durable, molded plastic. However, much of the equipment utilized for these purposes has remained constant for decades with little modification. Such equipment is often not customizable to a user's unique anatomy or physical structure; and if available, such customization is often costly and unable to be done at a convenient location, such as home or the athletic field, or the like. Furthermore, where such customization does exist, it is conventionally a single use device only capable of being molded once and may break following the application of force. There exists a need in the art for customizable protective equipment, guards, braces, etc., where the customization is user friendly, reformable, and capable of being conducted at a convenient location.

SUMMARY

Various pieces of customizable protective equipment, guards, etc. and methods for their use by a user are described herein. These pieces of protective equipment, guards, braces, etc. are capable of being quickly and easily customized. In one aspect a moldable portion for use as at least a part of a guard, including: a thermoplastic semi-crystalline propylene ethylene copolymer having a crystallinity of about 2% to about 65% making up between about 85% to about 99% of the moldable portion, where the thermoplastic semi-crystalline propylene ethylene copolymer is a chiral metallocene catalyzed copolymer of propylene and ethylene; a microwave susceptor making up about 1% to about 15% of the moldable portion; and wherein the moldable portion is adapted to be customized to an area of a user's anatomy it is intended to protect, and where the moldable portion is prepared for customization by heating to a temperature of about 60° C. to about 100° C.

In some embodiments, the moldable portion may be coupled with an outer layer to form the guard. In other embodiments, the moldable portion may be enveloped by a sleeve to form the guard.

In some embodiments, the thermoplastic semi-crystalline propylene ethylene copolymer may be Vistamaxx™ 3000; in other embodiments, the thermoplastic semi-crystalline propylene ethylene copolymer may be a blend including between about 1% and about 99% Vistamaxx™ 3980L and between about 1% to about 99% Vistamaxx™ 6102.

In some embodiments, the microwave susceptor is carbon black.

In some embodiments, the moldable portion may additional include a foaming agent configured to generate air spaces in the thermoplastic semi-crystalline propylene ethylene copolymer.

In some embodiments, the moldable portion may remain moldable for about 2 to 3 minutes as the temperature falls below 60° C. following heating. The moldable portion may also be adapted to be reformed to an area of a user's anatomy it is intended to protect by reheating to a temperature of about 60° C. to about 100° C.

In another aspect, a customizable guard includes: a moldable portion and an outer layer coupled with the moldable portion; the moldable portion, including: a thermoplastic semi-crystalline propylene ethylene copolymer having a crystallinity of about 2% to about 65% making up between about 85% to about 99% of the moldable portion, where the thermoplastic semi-crystalline propylene ethylene copolymer is a chiral metallocene catalyzed copolymer of propylene and ethylene, and a microwave susceptor making up about 1% to about 15% of the moldable portion; the moldable portion may be adapted to be customized to an area of a user's anatomy it is intended to protect, and where the moldable portion may be prepared for customization by heating to a temperature of about 60° C. to about 100° C.

In some embodiments, the outer layer may be removably coupled with the moldable portion, where the moldable portion is further prepared for customization by decoupling from the outer layer. In some embodiments, the outer layer may be a sleeve configured to envelop the moldable portion. In such embodiments, the sleeve may include a first exterior surface to contact the user and a second exterior surface to face outward relative to the user, and the moldable portion may be placed within the first exterior layer and second exterior layer.

In some embodiments, the thermoplastic semi-crystalline propylene ethylene copolymer may be Vistamaxx™ 3000. In other embodiments, the thermoplastic semi-crystalline propylene ethylene copolymer may be a blend including between about 1% and about 99% Vistamaxx™ 3980L and between about 1% to about 99% Vistamaxx™ 6102.

In some embodiments, the microwave susceptor may be carbon black. In some embodiments, the moldable portion may additionally include a foaming agent configured to generate air spaces in the thermoplastic semi-crystalline propylene ethylene copolymer.

In some embodiments, the moldable portion may be adapted to be reformed to an area of a user's anatomy it is intended to protect by reheating to a temperature of about 60° C. to about 100° C.

In yet another aspect, a method of customizing a guard to a user's individual anatomy, the method including: obtaining a moldable portion, where the moldable portion includes: a thermoplastic semi-crystalline propylene ethylene copolymer having a crystallinity of about 2% to about 65% making up between about 85% to about 99% of the moldable portion, where the thermoplastic semi-crystalline propylene ethylene copolymer is a chiral metallocene catalyzed copolymer of propylene and ethylene, and a microwave susceptor making up about 1% to about 15% of the moldable portion; dry heating the moldable portion to a temperature of about 60° C. to about 100° C.; applying the moldable portion to an anatomical region of the user; and setting the moldable portion, thereby forming a set moldable portion.

In some embodiments, the method may additionally include reheating, by dry heating, the set moldable portion a temperature of about 60° C. to about 100° C., thereby forming a reformable moldable portion; applying the reformable moldable portion to an anatomical region of the user; and setting the reformable moldable portion.

Throughout this specification and the claims, the terms "guard", "protective equipment", "brace", or "pad" may be used interchangeably to indicate an apparatus for protecting a user either from injury or protecting an injured site and facilitating healing of the same.

When used in this specification and the claims as an adjective rather than a preposition, "about" means "approximately" and comprises the stated value and every value within 10% of that value; in other words, "about 100%" includes 90% and 110% and every value in between.

BRIEF DESCRIPTION OF THE DRAWINGS

FIG. 1A illustrates a guard disposed on an individual. FIG. 1B illustrates a cross-sectional view of the composition of the guard of 1A. FIG. 1C illustrates a cross-sectional view of another embodiment of a guard.

FIG. 2A illustrates a cross-sectional view of a guard composition consisting solely of a moldable portion. FIG. 2B illustrates a cross-sectional view of a guard composition consisting of three layers.

FIG. 10A is a rear perspective view of the pair of compression pants. FIG. 10B is a front perspective view of the compression pants of FIG. 10A.

FIG. 13A illustrates an embodiment of exemplary protective equipment worn by a catcher; FIG. 13B illustrates an embodiment of exemplary protective equipment worn by a batter; and FIG. 13C illustrates an embodiment of exemplary protective equipment worn by pitcher.

DETAILED DESCRIPTION

Overview

Protective equipment, guards, braces, or the like are critical to the safety of a user and/or for protecting an injured site or facilitating healing after an injury. Ideally such protective equipment, guards, braces, or the like should be tailored to each user's individual anatomy and capable of being reformed as an individual's anatomy changes (e.g. due to swelling or other changes during the healing process). Pieces of protective equipment, guards, braces, or the like may be at least partially constructed of a moldable portion formed of a polymer blend, which is discussed in further detail herein.

Figures 1A, 1B, 1C, 2A, 2B:
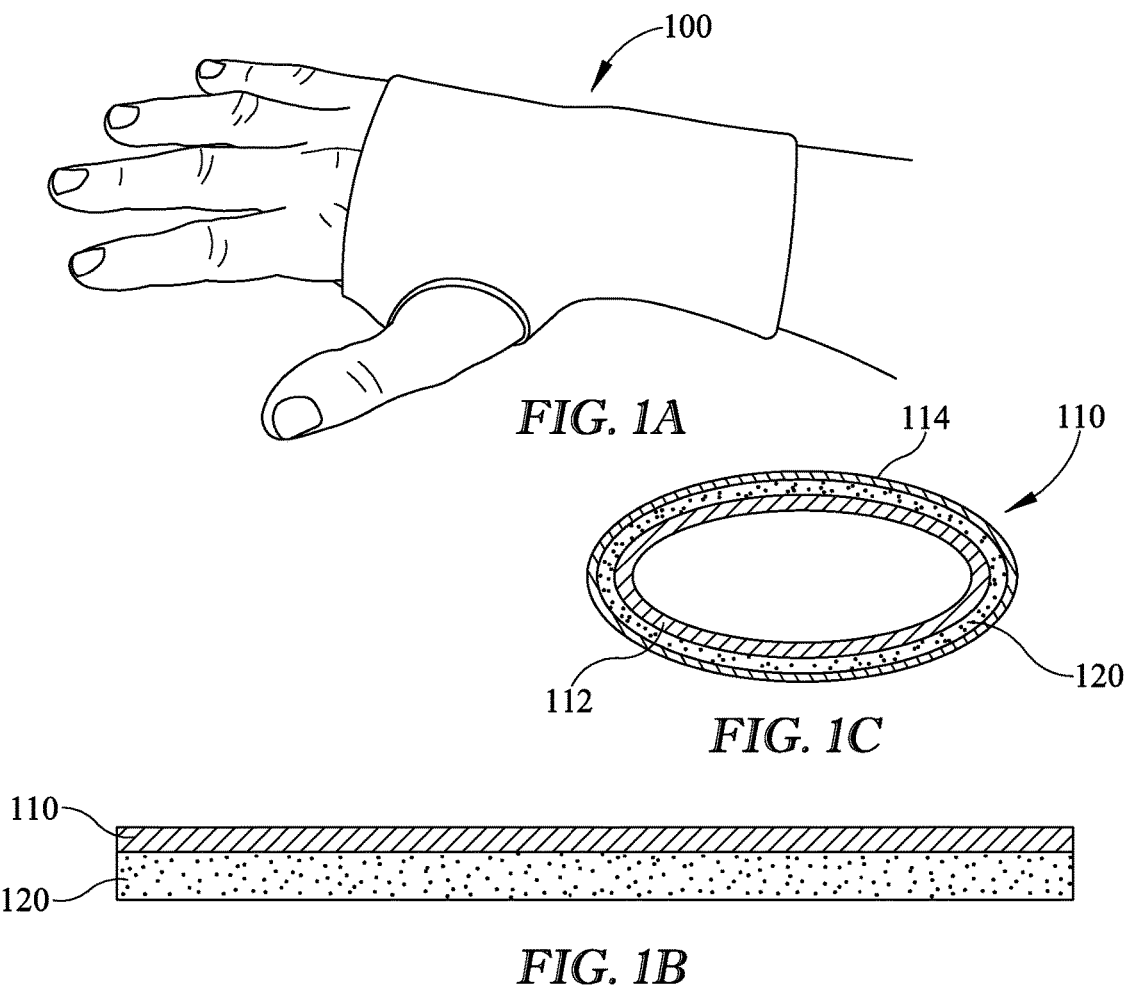
FIGS. 1A-C illustrate guards constructed at least partially of a moldable portion consistent with some embodiments of the invention.
FIGS. 2A-B illustrate of alternative embodiments of the composition of the guard.

An exemplary piece of protective equipment is illustrated in FIGS. 1A and 1B. It is to be expressly understood that other types of protective equipment, including other types of guards, for non-limiting example, helmets, braces, pads, splints, or the like may be used, many of which are discussed herein (see FIGS. 3-17). The descriptive protective guard 100 of the illustrative embodiment includes at least an outer layer 110 and a moldable inner layer 120, as best illustrated in FIG. 1B. The outer layer 110 may be a cover, or the like that is configured to couple with the moldable inner layer 120. In some instances, this outer layer 110 may be constructed of a soft, fabric material, such as a moisture wicking fabric (e.g. polyester, nylon, rayon, blends, neoprene, or the like). In other embodiments, the outer layer 110 may be constructed of hard, stiff material, such as a hard plastic, polycarbonate, etc. In some instances, the moldable inner layer 120 may be in direct contact with the user; while in other instances, the outer layer 110 may form a sleeve configured to envelop the inner moldable layer 120. In such instances, the outer layer 110 may comprise a first exterior surface 112, that may be placed in contact with the user, and a second exterior surface 114, that may be outward facing relative to the user, with a moldable inner layer 120 disposed within the first and second exterior layers 112, 114. In some instances the moldable inner layer 120 may be removable from the outer layer 110 for customization; while in other instances, the moldable inner layer 120 may be permanently coupled with the outer layer 110.

It is to be understood that the number of layers in the construction of a guard 100 described herein are not limited to the embodiments illustrated in FIGS. 1A-C, as illustrated in the cross-sectional views of FIGS. 2A-B. In some embodiments, the guard 100 may be constructed wholly of the moldable portion 120, as illustrated in FIG. 2A. In other embodiments, it may be desirable for the guard 100 to include a moldable inner layer 120, coupled with both soft outer layer 116 and hard outer layer 118, thus forming a three-layer construction, such as illustrated in FIG. 2B.

The moldable portion 120 is, as the name suggests, easily moldable to the anatomy of the particular user wearing it. Such a moldable portion may resist breakage and return to its molded shape upon application of a significant force or impact (e.g. a force equal to that of dropping a 45-pound weight on the moldable portion). Furthermore, the moldable portion may allow for subsequent reforming and adjustment of the guard to the anatomy of the user as desired. The moldable portion 120 of the guard may be heated in a microwave oven (described in detail herein) until it is moldable (e.g. is pliable for shaping). The moldable portion may be placed on a user and may be formed to the exact shape desired without use of additional materials or skills.

Composition of Moldable Portion

As stated, a guard consistent with the embodiments described herein may be or may include a moldable portion 120 (see FIGS. 1A-C). Such a moldable portion 120 may comprise a semi-crystalline polyolefin polymer (e.g. linear low density or high density polyethylene (PE), polyethylene terephthalate (PET), polytetrafluoroethylene (PTFE) or syndiotactic isotactic polypropylene (PP), etc.) or a polymer blend. The semi-crystalline polymer or polymer blend may be a thermoplastic polymer, such that the composition becomes pliable or moldable above a defined temperature (e.g. about 60° C. to about 100° C.) and solidifies upon cooling. In some instances, the semi-crystalline polyolefin polymer may be a low-density polymer. As a non-limiting example, the moldable portion 120 of the guard may include low-density polyethylene (LDPE), which, for example, may be defined by a density range of about 0.910 to about 0.940 g/cm3, and may also not be reactive at room temperatures. In other instances, a high density polypropylene (which may be defined by a range of about 0.93 to about 0.97 g/cm3) may also be used in combination with the low density polyolefin.

As a non-limiting example, the moldable portion 120 may include propylene-ethylene copolymers that are produced using a metallocene catalyst and activator, such as described in U.S. Pat. No. 6,525,157, which is hereby incorporated by reference. A copolymer produced this way, may include about 5% to about 25% by weight of ethylene-derived units and about 55% to about 75% by weight of propylene derived units.

Copolymerizing a propylene-ethylene copolymer may result in a semi-crystalline copolymer, which may be utilized in the moldable portion 120. Other thermoplastic polymer blends that be used in a moldable portion may also include an isotatic or syndiotactic polypropylene and an alpha olefin and propylene copolymer; in such instances the copolymer may include crystallizable alpha olefin sequences as described in U.S. Pat. Nos. 6,635,715 and 6,642,316, each of which is hereby each incorporated by reference.

As an additional non-limiting example, the moldable portion 120 may include bimodal propylene polymers such that those described in U.S. Pat. No. 10,287,372, incorporated by reference. For example, such a bimodal propylene polymer may have high porosity (e.g. greater than 15%) and/or low pore diameter (e.g. less than 165 µm). The propylene polymerization processes may use single site catalyst systems with supports with high surface area (e.g. greater than 400 m²/g), low pore volume (e.g. less than 2 mL/g), a specific mean pore diameter range of 1 mm to 20 nm, and high average particle size (e.g. greater than 30 µm).

It many instances, it may be desirable for the composition of the polymer blend to be altered depending on the particular type of guard or protective equipment within which the moldable portion 120 will be used. As an example, in some embodiments it may be desirable for the resulting moldable portion to be hard, so that it may resemble conventional hard, molded plastic protective equipment, guards, etc. While in other embodiments, it may be desirable for the resulting moldable portion to be soft, for example, so that the moldable portion 120 may have a springy rubber consistency. In still other instances, it may be desirable for the moldable portion 120 to be softer than known plastics utilized in protective equipment, guards, etc., but hard enough to absorb a substantial impact. In order to achieve a desired level of hardness, it may be desirable for the composition utilized in a moldable portion 120 to be formed by blending two or more copolymers, where each of the copolymers has a varied degree of hardness.

An exemplary blend that may produce a moldable portion 120 that is softer than known plastics utilized in guards and protective equipment, but hard enough to absorb an impact to the protective equipment may include about 2% to about 95% by weight of a first polymer component and about 98% to about 5% by weight of a second copolymer component. In some instances, the first copolymer may include an isotactic or syndiotactic polypropylene, which may have a melting point higher about 110° C., and in some embodiments a melting point between about 130° C. and about 171° C., which may be affected by the polymer's crystallinity. The first copolymer may also include copolymerized propylene and ethylene (utilizing a chiral metallocene catalyst system). The first copolymer may also have a crystallinity ranging from about 2% to about 65%, a propylene content ranging from about 75% to about 90% by weight, a melting point ranging from of from 50° C. to 105° C.

In other instances, the polymer blend may be an un-crosslinked blend. In some embodiments, the blend may include a dispersed and continuous phase of a crystalline polymer, which may be dispersed in phases less than about 3 µm by about 3 µm by about 10 µm in size. In other embodiments, the blend may include propylene units ranging from about 65% to about 100% by weight. In still other embodiments, the first and second polymers may contain stereoregular polymerized propylene units, and the copolymer blend may have a tensile elongation in excess of 650%.

In another example, the first polymer may be a propylene homopolymer with a melting point at or above about 115° C., and the second polymer may be a copolymer of propylene units. The second polymer may range from about 8% to about 25% ethylene units by weight, and may have a melting point at or less than about 100° C.

As an additional, non-limiting example, the polymer blend of the moldable portion 120 may include one or more grades of Vistamaxx™ produced by ExxonMobil of Houston, Tex. 77253. Table 1 includes a listing of various grades of Vistamaxx™ that may be used in the moldable portion and various respective properties, including ethylene content, Vicat softening point (ASTM D 1525), flexural modulus, and hardness (ASTM D2240) Shore D/A. The grades of Vistamaxx™ provided in Table 1 are merely illustrative, non-exhaustive, and should not be considered limiting.

TABLE 1

| Grade Name | Ethylene Content (weight %) | Vica Softening Point ASTM D 1525 ° C.(° F.) | Flexural Modulus - 1% Secant (psi) | Hardness 15 sec ASTM D2240 Shore D/A |
|---|---|---|---|---|
| 3588 | 4 | 103 (217) | 58400 | 50D (Very hard) |
| 3980FL | 9 | 77.3 (171) | 17000 | 34D (Hard) |
| 3000 | 11 | 65.0 (149) | 9050 | 27D (Soft/Hard) |
| 6502 | 13 | 51.4 (125) | 2960 | 71 (Soft) |
| 6102 | 16 | 53.0 (129) | 2090 | 67A (Soft) |

In some instances, it may be desirable to blend two or more grades of Vistamaxx™ at varying percentages in order to achieve a desired level of hardness and/or impact resistance of the composition of the moldable portion 120.

It may be desirable, in some instances, for any of the compositions of the moldable portions 120 described herein to additionally include one or more foaming agents. For example, the use of a foaming agent may result in the reduction in use of raw material (e.g. polymer blends), which may decrease cost and the resulting moldable portion's carbon footprint. In some instances, the use of a foaming material may reduce the amount of polymer required by as much as 50%. Foaming agents may be used in order to introduce foaming, resulting in a polymer foam with air bubbles or tunnels disposed therein. These polymer foams may be either closed-cell or open-cell. Generally, closed-cell foams exhibit more rigidity, while open-cell foams tend to be more flexible.

For example, such a foaming agent may be a decomposable chemical foaming agent, which at elevated temperatures decompose to form gases or vapors allowing the polymer foam to form. Both organic and inorganic foaming agents may be used with the polymer blend. For example, organic foaming agents may include, but are not limited to: 4,4'-oxybis benzene sulfonyl hydrazide; azodicarbonamide; azobisformamide; azobisisobutyronitrile; diazoaminobenzene; N,N-dimethyl-N,N-dinitroso terephthalamide; N,N-dinitrosopentamethylene-tetramine; benzenesulfonyl-hydrazide; benzene-1,3-disulfonyl hydrazide; diphenylsulfon-3-3, disulfonyl hydrazide; p-toluene sulfonyl semicarbizide; barium azodicarboxylate; butylamine nitrile; nitroureas; trihydrazino triazine; phenyl-methyl-uranthan; p-sulfonhydrazide; and/or peroxides. Inorganic foaming agents may include, but are not limited to: ammonium bicarbonate and/or sodium bicarbonate. In other instances, Ecocell® produced by Polyfil, Rockaway, N.J. 07866, may be used as a foaming agent in the composition of the moldable portion.

In some embodiments, additional polymers (e.g. elastomers, plastomers, rubber, etc.) may be mixed with the propylene-ethylene copolymer (including one or more of the various grades of Vistamaxx™) in order to change and/or enhance various properties of the co-polymer. For example, the addition of an elastomer, which is a polymer with viscoelasticity, may increase the ease with which the moldable part is molded to the anatomy of the user.

In some embodiments, it may be desirable for a guard to be constructed of two separate components, where each component may be a moldable portion described herein. In such instances, it may be desirable to have harder shell component and a softer core component for a guard. Such a construction may be particularly advantageous in guards where a hard outer component is typically used to absorb the bulk of an impact and a softer guard to further protect the site from injury. As a non-limiting example, a shin guard (see FIG. 13) may have an outer shell constructed of a hard moldable portion (e.g. Vistamaxx™ 3980FL) and a softer inner core constructed of a softer moldable portion (e.g. Vistamaxx™ 6102). As other example, shoulder pad systems such as those used in American football (see FIG. 8) may be similarly constructed with a hard outer moldable portion and a softer inner core.

In some embodiments, particularly embodiments where the molded portion of the guard or protective equipment may be visible to an user or third party (e.g. members of a crowd, coaches, or the like), one or more colorants, glitter components, or the like may be added to the copolymer in order to achieve a desirable aesthetic appearance, such as displaying team colors.

In some instances, the moldable portion (or in some embodiments, the entire guard) may be heated until moldable, meaning the moldable portion is pliable for shaping by the user without any additional equipment, through the use of a microwave oven. It is known that microwaves do not typically interact with most polymer compositions, it is for this reason water has typically been used during microwave heating of polymers or polymer blends. For example, in some instances a polymer or polymer blend may be placed in a water bath in the microwave oven or wrapped in a wet cloth prior to placing in the microwave oven.

However, in some instances it may be desirable, for example for ease of use by the user for a dry heat (e.g. without the use of water in the heating process) to be used. In such instances, the moldable portion may additionally include a microwave susceptor that allows the moldable portion to absorb the microwaves. Generally, a susceptor may be a material used for its ability to absorb electromagnetic energy and convert it to heat. In addition to the polymer or polymer blend, the composition of the moldable portion may in some instances, include between 1% and 15% microwave susceptor. Where the moldable portion has a larger amount of a microwave susceptor the reaction to the microwave activity may increase, and therefore heating intensified. Where the moldable portion has a smaller amount of a microwave susceptor the reaction to the microwave activity may be decrease, and therefore the heating may be less intense. More specifically, in some instances the composition of the moldable portion may be about 5% microwave susceptor. In some instances, the microwave susceptor may be a carbon structure, such as carbon black, carbon fibers, carbon nanotubes, graphene. In other instances, the microwave susceptor may include various conductive or magnetic materials (e.g. metals, metal salts, metal oxides, zeolites, hydrated minerals, hydrated salts of metal compounds, polymeric receptive materials, clays, silicates, ceramics, sulfides, titanates, carbides, sulfur, inorganic solid acids or salts, polymer acids or salts, inorganic or polymeric ion exchangers, clays modified with microwave-receptive compounds, etc.).

Moldable portions of the various compositions described herein may possess certain characteristics that are desirable in a piece of protective equipment, guard, brace, or the like. For example, as described previously herein, the moldable portion may be capable of being heated in a microwave oven and formed and reformed a second, third, and so on times, allowing for adjustment to the equipment, guard, etc. For example, this reforming may be desirable to correct an initial poor fit, to allow for a change in fit as an injury heals, or to allow for change in fit as a wearer grows (particularly relevant where the user is a child or adolescent), or any other situation for reformation may be desirable. As another example, the moldable portion may be impact resistant or shock absorbing. This may be particularly desirable where the moldable portion is incorporated into a piece of equipment, guard, etc. for use in a contact sport (e.g. football, lacrosse, etc.), where impacts are common and desired to be protected against. Furthermore, the moldable portion described herein may be capable of breakage and return to its molded shape upon application of a significant force or impact (e.g. a force equal to that of dropping a 45-pound weight on the moldable portion). In contrast, typical guards may break or shatter upon the application of significant force.

Application of Moldable Portion to Individual

In order to apply the moldable portion and/or guard to a user, the moldable portion must be heated in order to become pliable enough to mold around the anatomy of the wearer. In some instances, particularly when moldable portion includes a microwave susceptor as described herein, the moldable portion may be heated in a microwave oven for about 2 to about 3 minutes on the microwave oven's high heat setting in order to achieve a desired pliability. In other instances, the moldable portion (or in some instances, the entire guard)

may be placed in a moist towel (e.g. a paper towel or a hand towel) and heated in a microwave oven for about 30 to about 90 seconds until moldable. In still other instances, the moldable portion may be placed into a liquid medium, (e.g. water) at a temperature ranging from about 60° C. to about 100° C. The quantity of the liquid medium (e.g. water) may be sufficient to full cover or submerge the moldable portion. For example, a hot water bath may be utilized. The moldable portion may remain in the liquid medium for a few seconds, or until moldable.

For example, the desirable pliability may be achieved above a temperature of about 60° C. to about 100° C. It is to be understood that the times provided are merely estimates, and that the time required to heat the moldable portion may vary, particularly based on the wattage of the microwave oven used. For example, a higher wattage microwave oven may require a shorter heating time, while a lower wattage microwave oven may require a longer heating time. Heating may be complete when the moldable portion is pliable enough to mold around a user's anatomy, but not near liquid consistency.

Prior to placing the moldable portion directly on the user, the moldable portion may be cooled for a brief period of time, for example a few seconds. This cooling period should only be long enough to allow the moldable portion to cool to a temperature that will not burn or otherwise cause discomfort to a user. After cooling, the moldable portion may be placed on the desired anatomical surface for customization, for example, on the user's wrist, ankle, neck, shoulders, thighs, head, or any additional location where a guard or piece of protective equipment may be placed. In some instances, the moldable portion may be set into the desired formation by leaving the moldable portion in place on the user until no longer moldable. The moldable portion may also be removed and allowed to set at ambient conditions; alternatively, to accelerate the setting/hardening process the moldable portion may be placed in a cold-water bath until set and no longer moldable.

Additional Embodiments of Guards

The moldable portion described herein may be utilized in any number of types of guards or pieces of protective equipment, and should not be understood to be limited to the embodiment illustrated in FIG. 1A.

Figure 3:
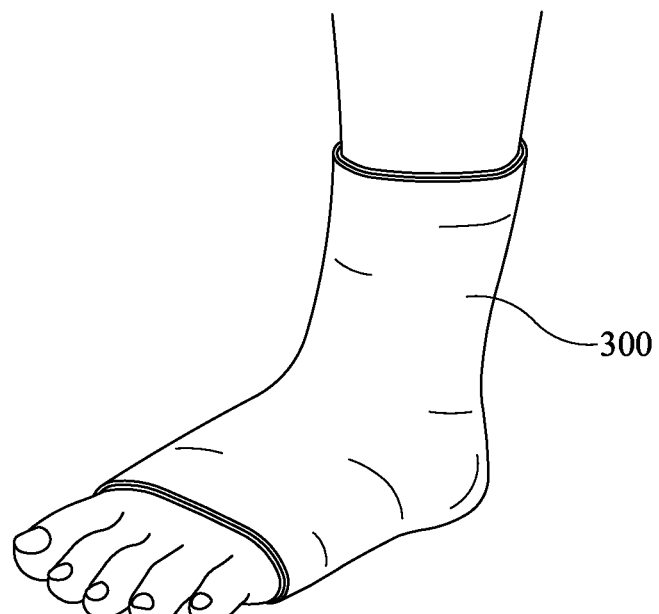
FIG. 3 illustrates a perspective view of an exemplary ankle brace consistent with some embodiments of the invention.
Figure 4:
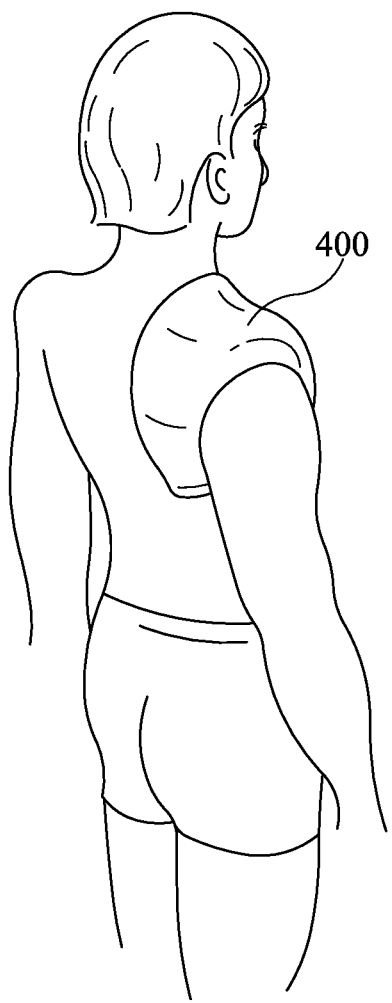
FIG. 4 illustrates a perspective view of an exemplary shoulder guard consistent with some embodiments of the invention.
Figure 5:
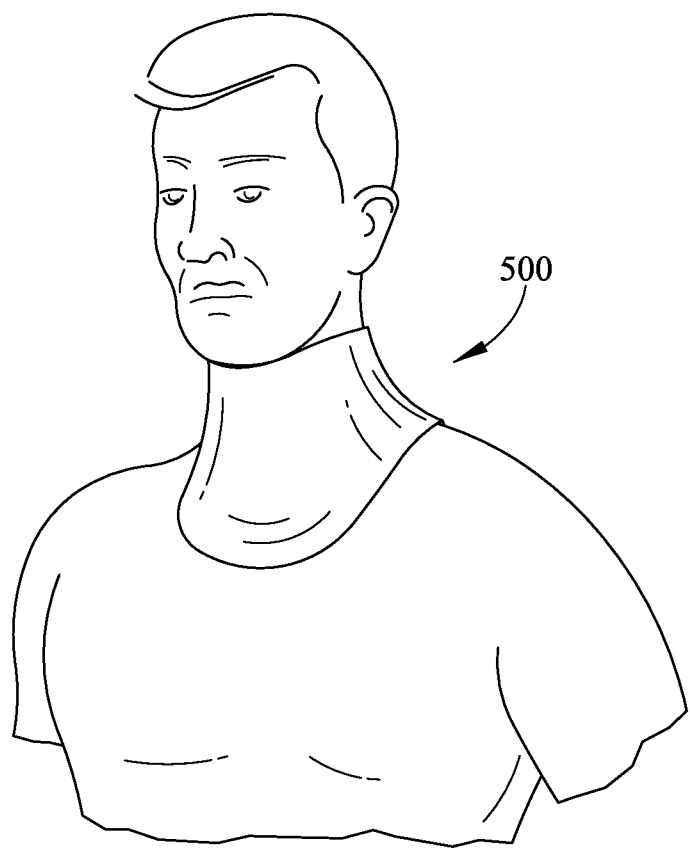
FIG. 5 illustrates a perspective view of an exemplary neck brace consistent with some embodiments of the invention.

In some embodiments, the moldable portion may be, or be incorporated into a brace, guard or the like for use with an injury. For example, an ankle brace 300 is illustrated in FIG. 3. The ankle brace may comprise a wrap type brace or alternatively incorporate a more rigid ankle brace structure. In other embodiments, the moldable portion may be, or be incorporated into a shoulder pad/sling 400, such as illustrated in FIG. 4. In still other embodiments, the moldable portion may be, or be incorporated into a neck brace 500. Although the ankle brace 300, shoulder pad 400, and neck brace 500 are each illustrated as a single pad, this is not to be understood as limiting, as the brace, guard, or the like may comprise multiple padding sections that may include the moldable portion.

Figure 6:
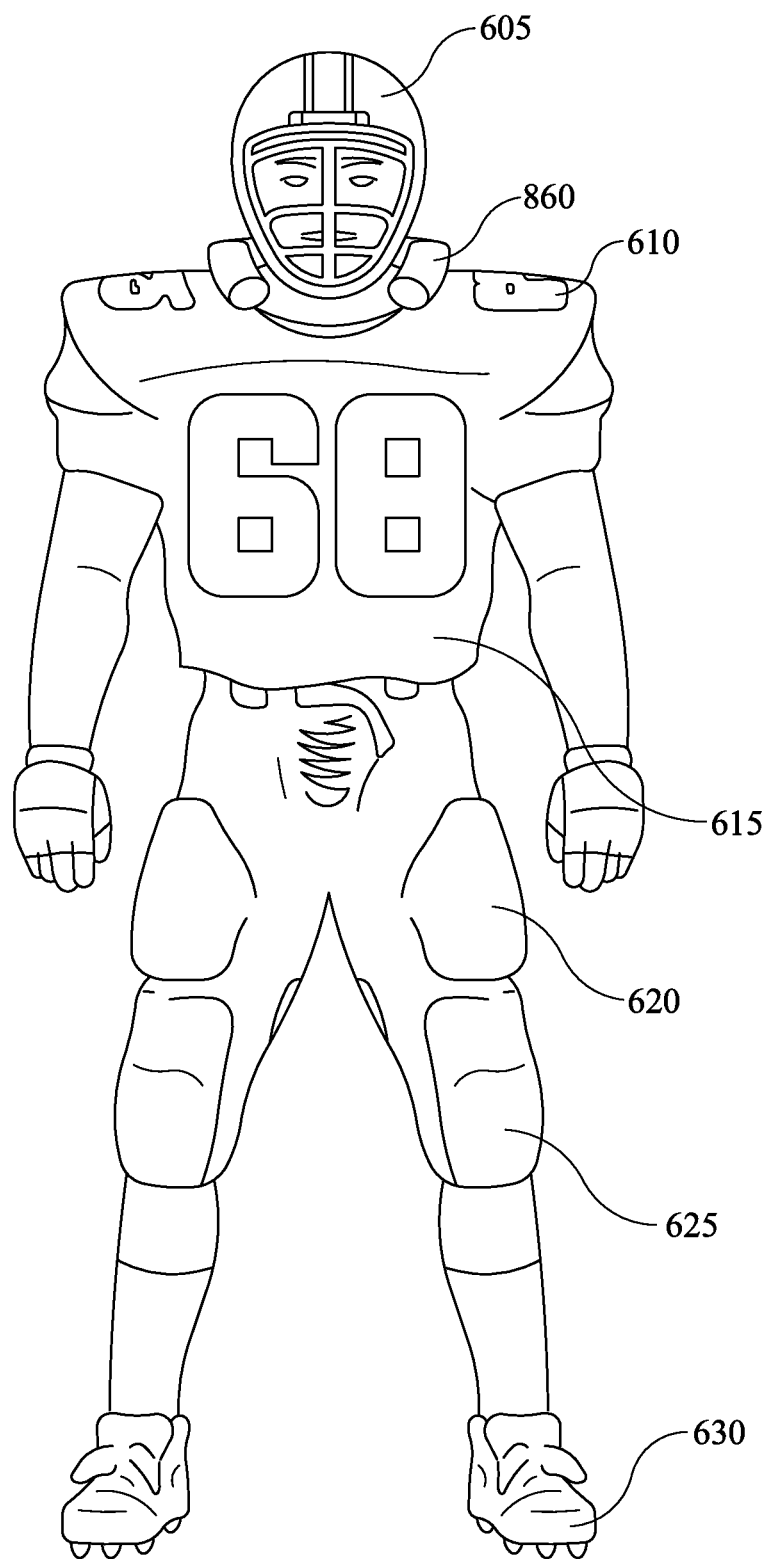
FIG. 6 illustrates exemplary pads and protective equipment utilized by American football players consistent with some embodiments of the invention.
Figure 7:
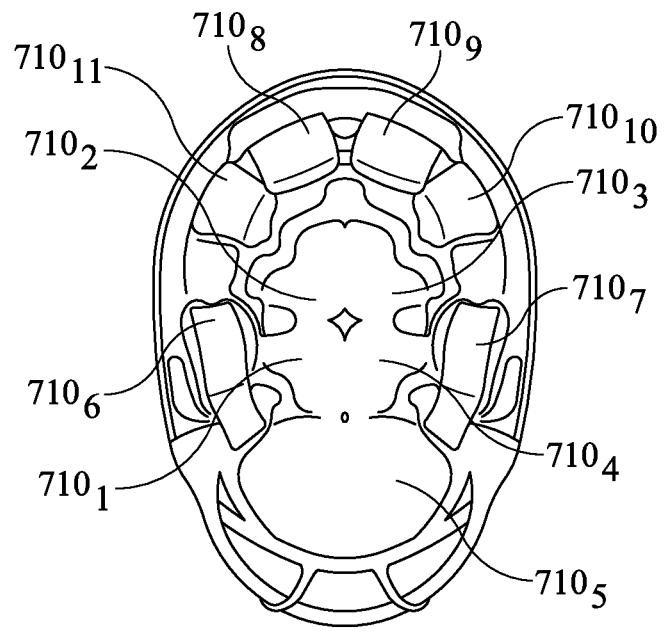
FIG. 7 illustrates a bottom view of an exemplary American football helmet consistent with some embodiments of the invention.

In other embodiments, the moldable portion may be, or be incorporated into, a piece of protective equipment utilized in athletics. For example, FIG. 6 illustrates a non-limiting example of the various types of protective equipment typically utilized by American football players that may include the moldable portion described herein. Such equipment may include, but is not limited to: a helmet 605, shoulder pads 610, padded jersey and/or under jersey padding 615, thigh pads 620, knee pads 625, and cleats 630. More specifically, illustrated in FIG. 7 is an embodiment of an American football helmet. This helmet contains a plurality of pads $710_{1-n}$ positioned therein to minimize the risk of injury, in particular the risk of concussive injury, to an athlete. Each pad, or pad type, may serve to protect a different area of the head and brain. For example, a plurality of pads $710_1$, $710_2$, $710_3$, $710_4$ may protect the top of the head; one or more pads $710_5$ may protect the front of the head or forehead region; one or more pads $710_6$ and $710_7$ on each side of the helmet may protect the jaw; and a plurality of pads $710_8$, $710_9$, $710_{10}$, $710_{11}$ may protect the back of the head. In some embodiments, at least one of these pads is a removable and moldable portion that may be custom fitted, as described herein, and then reinserted into the helmet. In other embodiments, the entire helmet may be heated (for example by insertion in an oven) and then applied to the head for customization to the individual athlete. In some embodiments, all of the interior pads 710 of the helmet are moldable portions comprised of the polymer blend described further herein; while in other embodiments, the padding may be a mixture of the polymer blend and other, more traditional pads known in the art. Furthermore, it is to be understood that the layout and/or number of the padding illustrated in FIG. 7 is merely exemplary, and that in some instances the padding placement and/or number may be slightly different, in particular based on the size of the helmet and the age of the athlete for which it is intended. Still further, it should be understood that the shapes of the pads depicted in FIG. 7 should not be considered limiting and that other shapes may be utilized. According to some non-limiting embodiments, the pads 710 may be removably retained in a plurality of forms including, but not limited to snaps, pockets, hook-and-loop fasteners, belts or straps and others.

Figure 8:
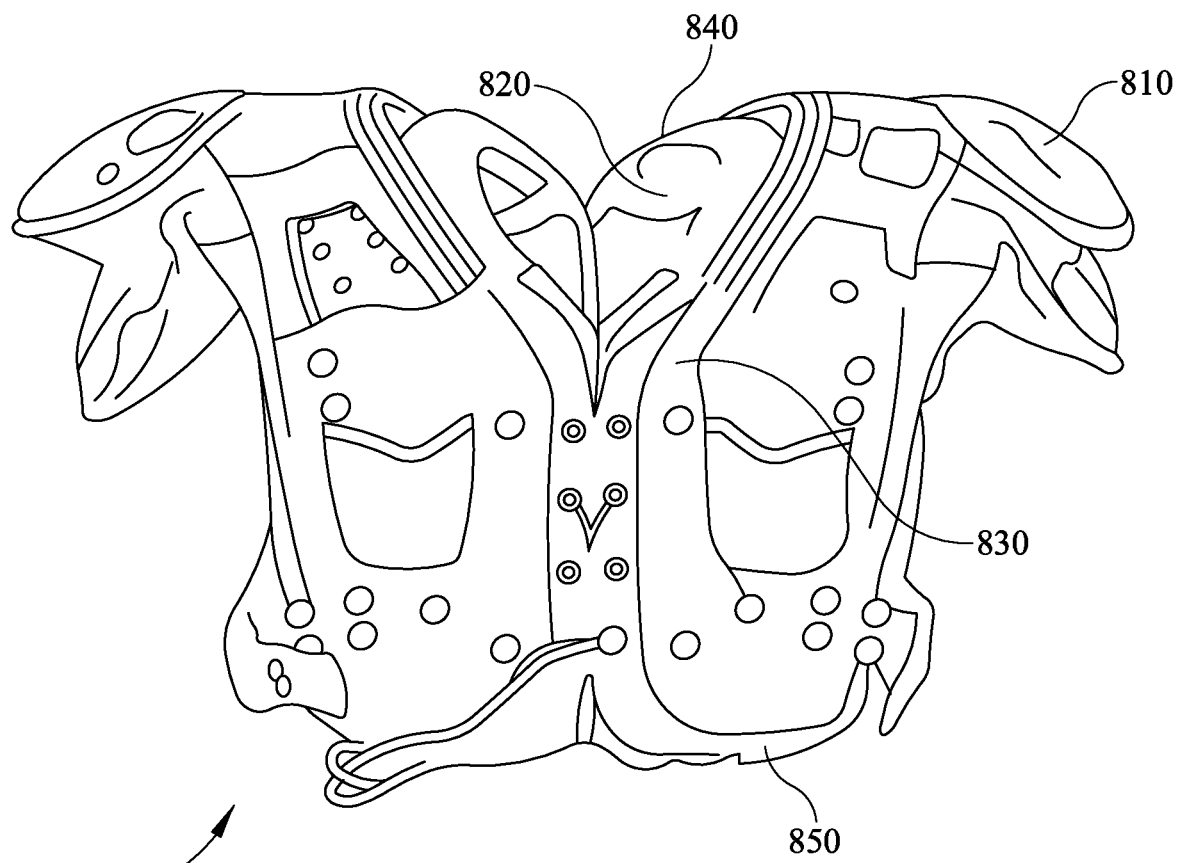
FIG. 8 illustrates a front perspective view of an exemplary shoulder pad system used in American football consistent with some embodiments of the invention.

Turning now to FIG. 8, which illustrates an exemplary embodiment of a shoulder pad system 800 utilized in American football. This shoulder pad system 800 includes various shell pieces 810 that traditionally are constructed of a hard material, such as plastic. However, in some instances, these shell pieces 810 may be constructed of a hard form of the polymer described herein. These shell 810 pieces may function to spread the force of an impact to an athlete out to the padding 820 positioned underneath the shell pieces 810, which function to absorb the shock of the impact. In some embodiments, the shoulder pad system 800 may also include a chest protector 830 and one or more back plates 840. The shoulder pad system may also optionally include an abdominal pad (not illustrated in FIG. 8); in some instances such an abdominal pad may be attached to a lower portion 850 of the shoulder pad system 800, in other instances the abdominal pad may be included as an integral part of the shoulder pad system 800. The shoulder pad system 800 may also optionally include a neck roll 860, such as illustrated in FIG. 6. In some instances, the neck roll 860 may be integrally connected with the shoulder pad system 800 (see FIG. 6); while in other instances the neck roll 860 may be removably affixed to the shoulder pad system 800. The shoulder pad system 800 may also include one or more rib guards (not visible in FIG. 8). In some embodiments, at least one of the pads 820 of the shoulder pad system 800 is a removable and moldable portion that may be custom fitted, as described herein, and then reattached to the shoulder pad system 800. The pad 820 may be disposed beneath the outer shell pieces. The pads 820 may be removably retained, but not limited to, snaps, pockets, hook-and-loop fasteners, belts or straps and the like. In other embodiments, the entire shoulder pad system 800 may be heated (for example in an oven) and then applied to the shoulders and torso for customization to the individual athlete's anatomy. In some embodiments, all of the pads 820 of the shoulder pad system 800 are moldable portions constructed of the polymer blend described herein; while, in other embodiments, the pads 820 may be a mixture of the polymer blend and other, more traditional pads known in the art. It is to be understood that FIG. 8 is merely an exemplary embodiment of a shoulder pad system, and is not to be understood as limiting. The placement and/or number of pads in a shoulder pad system may vary. Further, the shapes of the pads may also vary depending on the size or other factors of the pad system 800.

Figure 9:
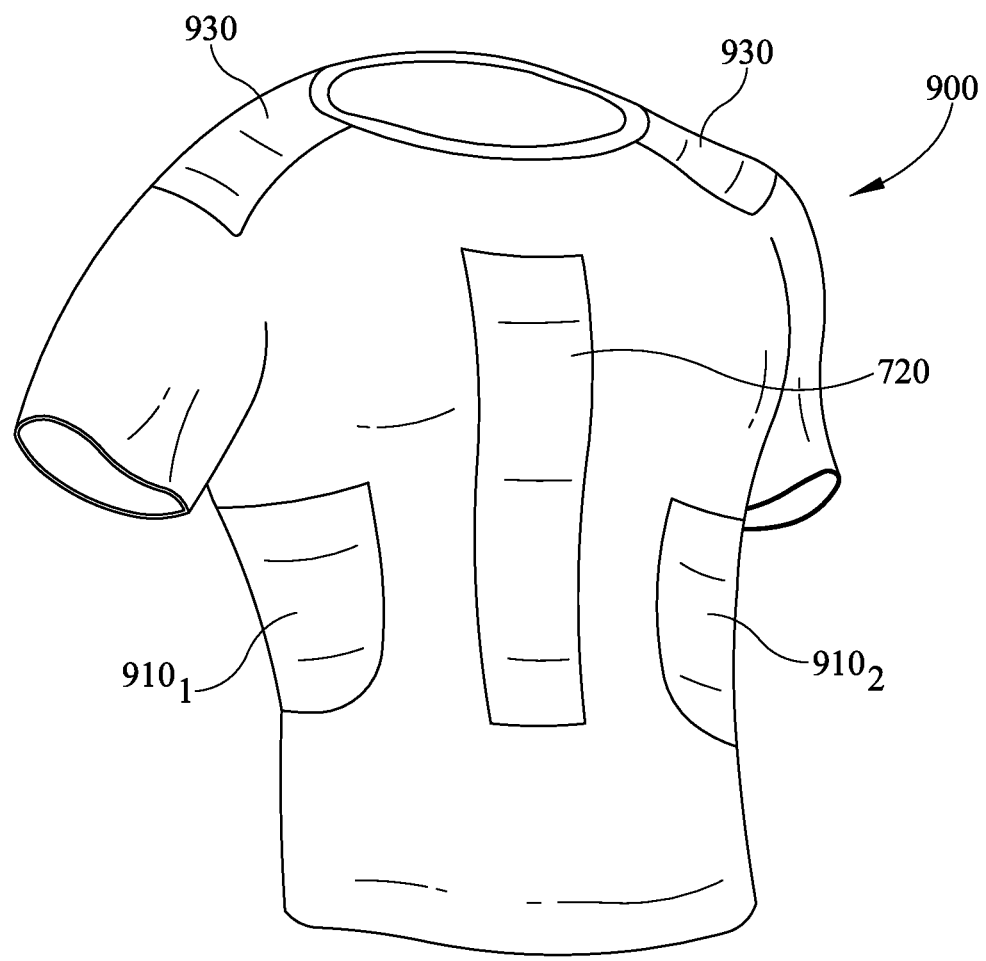
FIG. 9 illustrates a rear perspective view of an exemplary compression shirt consistent with some embodiments of the invention.

Turning now to FIG. 9, a rear view of a padded compression shirt 900, which may be worn under an athlete's jersey, is illustrated. Compression shirts, such as the embodiment illustrated in FIG. 9, are often utilized to provide additional impact protection to an athlete without impeding flexibility. In the embodiment illustrated in FIG. 9, the compression shirt 900 includes a first rib pad $910_1$ and a second rib pad $910_2$, a spine pad 920, and a first clavicle pad $930_1$ and a second clavicle pad $930_2$. In some embodiments, at least a portion of each of the rib padding $910_1$, $910_2$, a spine pad 920, and clavicle pads $930_1$, $930_2$ of the compression shirt 900 are moldable portions comprised of the polymer blend described herein; while in other embodiments, the padding may be a mixture of the polymer blend and other padding known in the art.

In some embodiments, the moldable portions may be permanently affixed to the compression shirt 900 as the entirety or part of a pad (e.g. the first or second rib pads $910_1$, $910_2$, spine pad 920, and/or the first or second clavicle pad $930_1$, $930_2$). In other embodiments, the moldable portions may be removable, for example they may be contained within a pocket such that they may be removed and prepared for customization and then replaced. In such embodiments, the combination of the moldable portion and the pocket, which may or may not have additional padding, may include a pad (e.g. the first or second rib pads $910_1$, $910_2$, spine pad 920, and/or the first or second clavicle pad $930_1$, $930_2$). Furthermore, it is to be understood that the specific layout and/or number of the pads illustrated in FIG. 9 is merely exemplary, that in some instances the padding placement and/or number may be slightly different, and there may be more or less pads. Likewise, shapes of the pads may be different and still be within the scope of the instant embodiments. For example, whereas spine pad 920 is depicted as a single pad, the spine pad 920 may be defined by two or more pads. Further, as with previous embodiments, the pads of the compression shirt 900 may be removably retained in a variety of ways previously described or in other manners. This is not to suggest that other types of shirts could not be used as the description of compression shirts is merely illustrative and other types of shirts may be utilized and comprise padding.

Figure 10A:
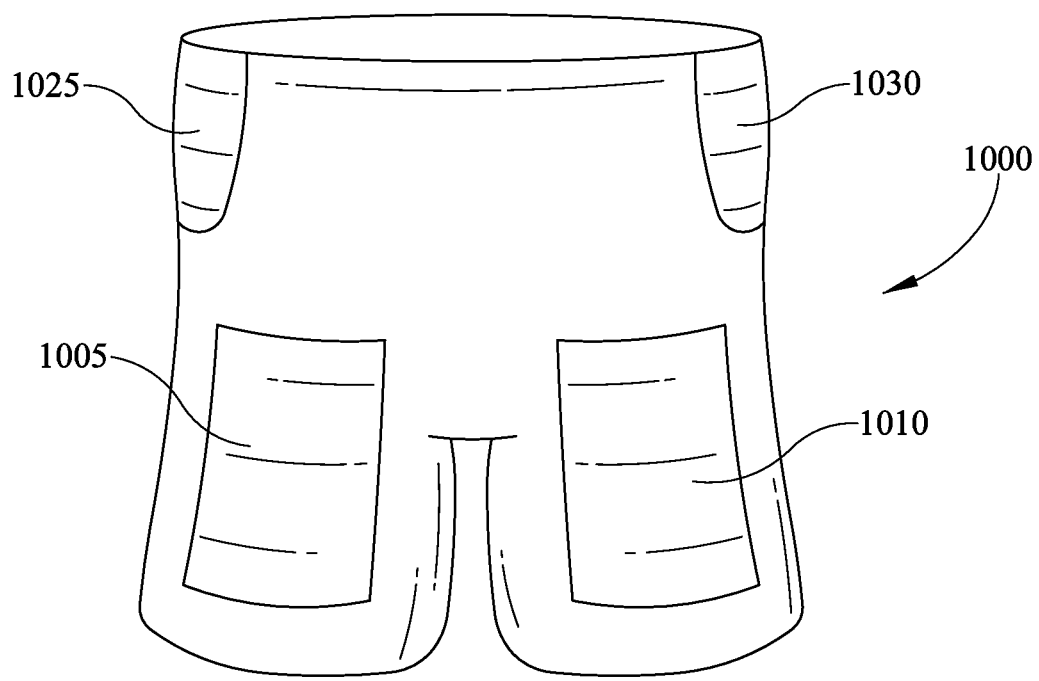
FIGS. 10A-B illustrate an exemplary pair of compression pants consistent with some embodiments of the invention.
Figure 10B:
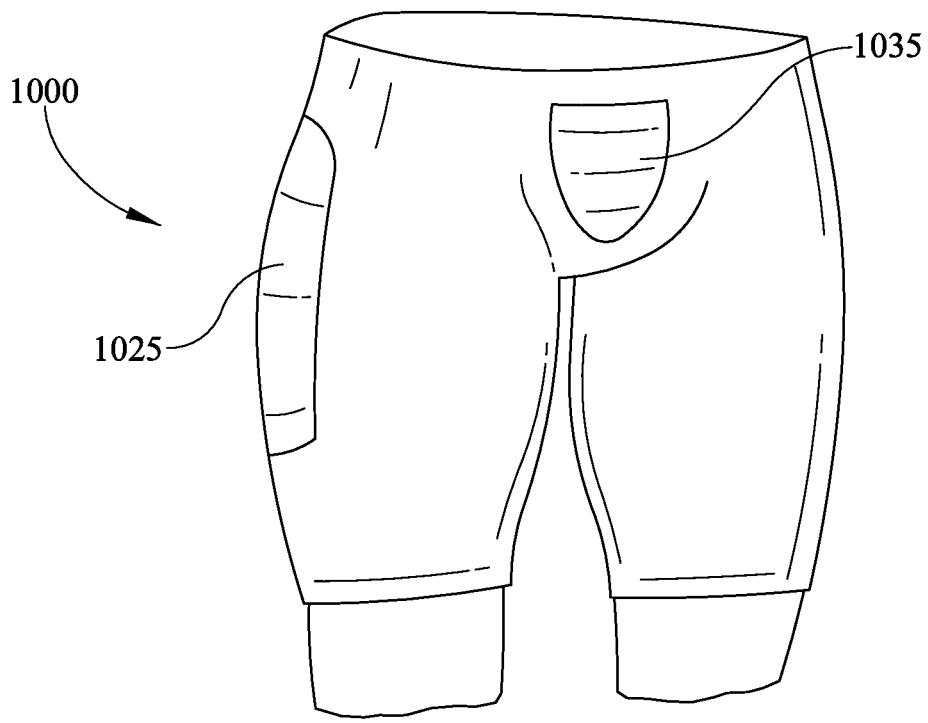

Referring now to FIG. 10A-B, a front (FIG. 10A) and a rear (FIG. 10B) view of an exemplary pair of compression pants 1000 are illustrated. In American football these compression pants typically have a plurality of pads to protect the thighs, knees, hips, and/or tail bone of the athlete. As an example, FIG. 10A illustrates the front of a pair of compression pants 1000, where a first thigh pad 1005 and a second thigh pad 1010 are visible. In some embodiments, the compression pants may also include a first hip pad 1025 and a second hip pad 1030 for protecting the hips from impact. Referring now specifically to the FIG. 10B, the compression pants may further include a tail pad 1035 that provides additional protection to the buttocks and tail bone. In some embodiments, at least a portion of each of the thigh pads 1005, 1010, hip pads 1025, 1030, and tail pad 1035 of the compression pants 1000 may be moldable portions comprised of the polymer blend described herein; while in other embodiments, the padding of the compression pants 1000 may be a mixture of the polymer blend and other, more traditional pads known in the art. Furthermore, as with previous embodiments, it is to be understood that the specific layout and/or number of the pads illustrated in FIG. 10 is merely exemplary, that in some instances the padding placement and/or number may be slightly different, and there may be more or less pads. For example, some embodiments of compression pants 1000 may not include hip pads 1025, 1030 or a tail pad 1035; while other embodiments the compression pants may additionally include knee pads (not illustrated in FIGS. 10A-B).

In some embodiments, the moldable portions may be permanently affixed to the compression pants 1000 as the entirety or part of a pad (e.g. the thigh pads 1005, 1010, hip pads 1025, 1030, and/or tail pad 1035). In other embodiments, the moldable portions may be removable, for example they may be contained within a pocket such that they may be removed and prepared for customization and then replaced. In such embodiments, the combination of the moldable portion and the pocket, which may or may not have additional padding, may comprising a pad (e.g. the thigh pads 1005, 1010, hip pads 1025, 1030, and tail pad 1035). Furthermore, it is to be understood that in some embodiments the pants may, in other embodiments, extend all the way to the ankle and include additional padding (e.g. knee pads, etc.).

Although primarily described herein in terms of equipment and padding utilized in American football, the use of moldable portions in athletic protective equipment is not so limited. Moldable portions comprised of the blended polymer described herein may be utilized in protective equipment for hockey, lacrosse (see FIG. 11), soccer (see FIG. 12) or any other type of contact sport. Additionally, the moldable portions may be utilized in protective equipment for non-contact sports, such as baseball (see FIG. 13), various snow sports (e.g. snowboarding), in-line skating, skateboarding (see FIG. 14), or the like.

Figure 11:
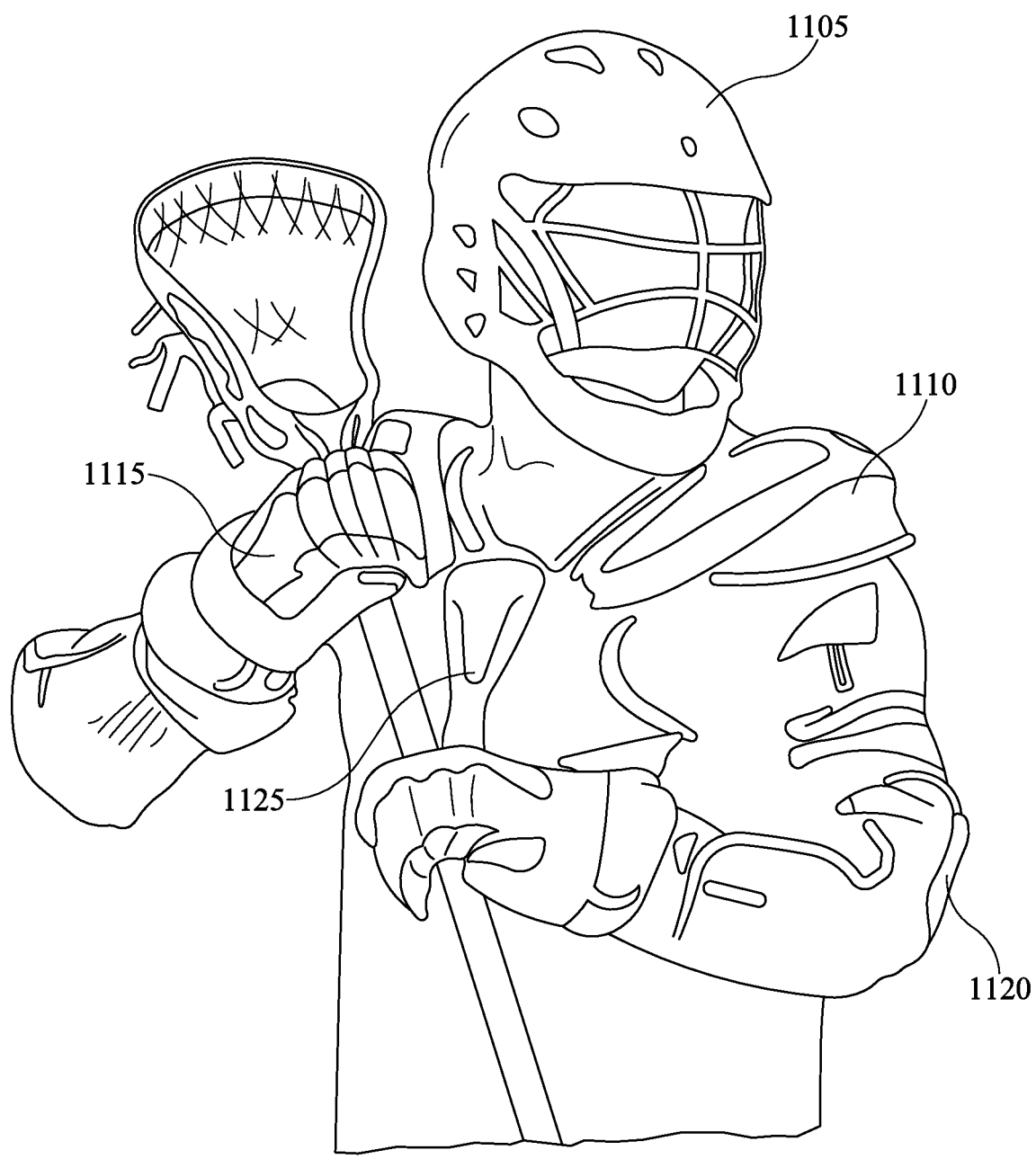
FIG. 11 illustrates an embodiment of exemplary pads and protective equipment utilized by lacrosse players consistent with some embodiments of the invention.

FIG. 11 illustrates a non-limiting example of some various types of protective equipment typically utilized by lacrosse players. Such equipment may include, but is not limited to: a helmet 1105, shoulder pads 1110, gloves 1115, arm protection 1120 (including elbow pads), and/or rib pads 1125. Any, or all, of the pads included in these protective pieces may be and/or may include a moldable portion that is comprised of a mixture of the polymer blend described herein.

Figure 12:
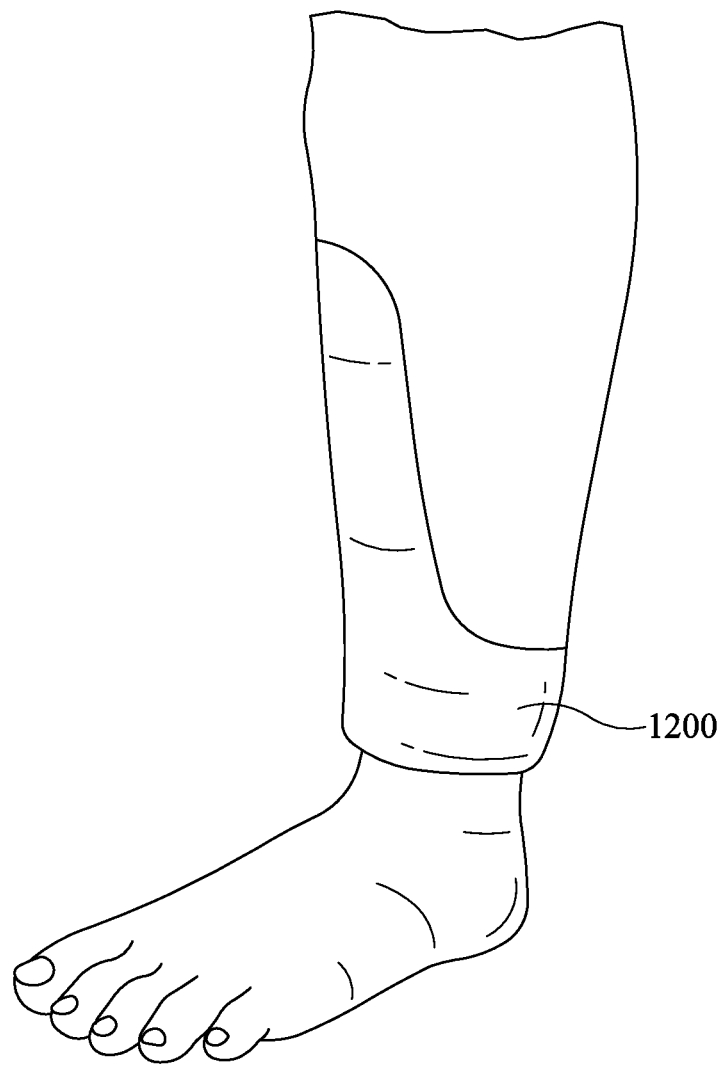
FIG. 12 illustrates a perspective view of an exemplary shin guard consistent with some embodiments of the invention.

As another illustrative example, the moldable portion that is comprised of a mixture of the polymer blend described herein may be, or be incorporated into, a shin guard 1200 (for example as used in soccer), as illustrated in FIG. 12.

Figures 13A, 13B:
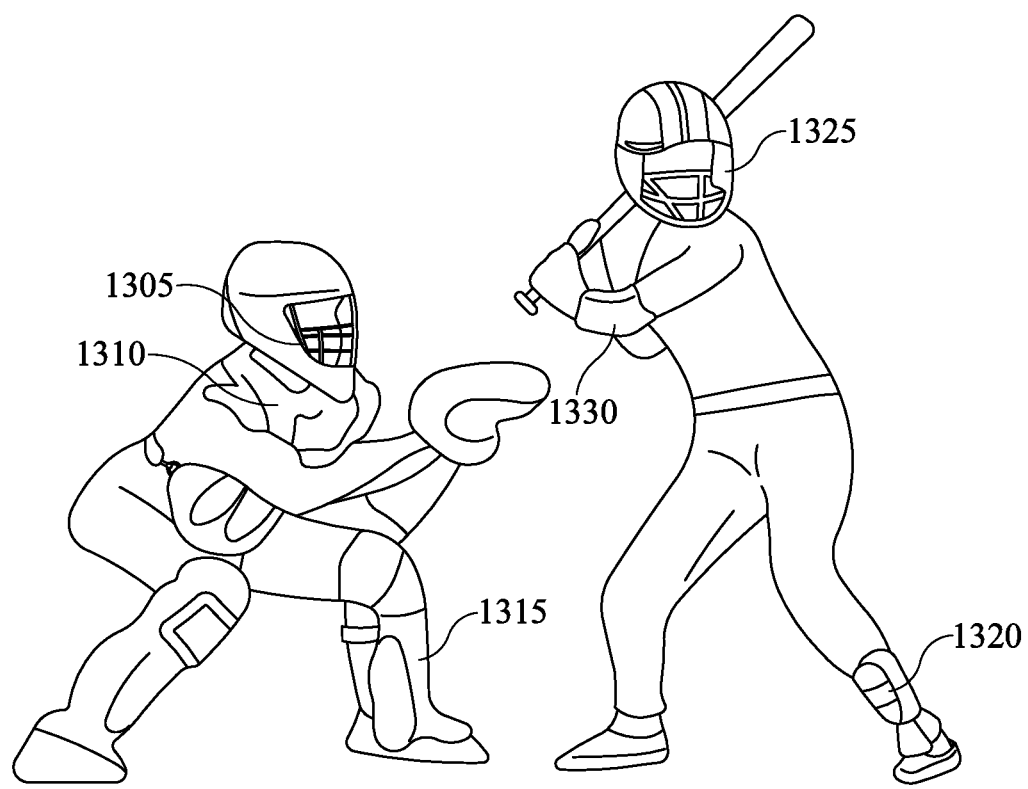
FIGS. 13A-C illustrates an embodiment of exemplary pads and protective equipment utilized by baseball players consistent with some embodiments of the invention.
Figure 13C:
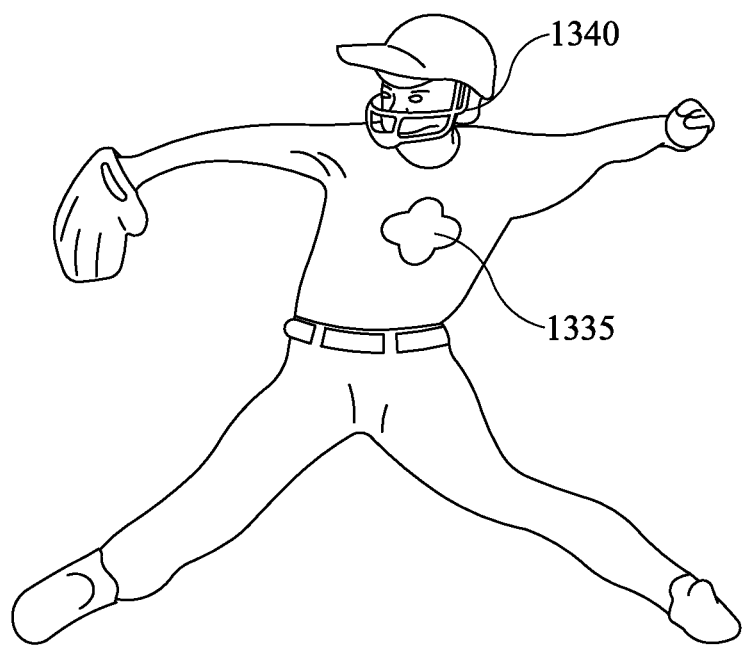

FIGS. 13A-C illustrate a non-limiting example of some various types of protective equipment typically utilized by baseball players. FIG. 13A illustrates such protective equipment typically worn by a catcher, including, but not limited to: a face mask 1305; a chest protector 1310; and one or more shin guards 1315. In some embodiments, the face mask 1305 of a pitcher may also include a throat guard and a helmet. FIG. 13B illustrates such protective equipment typically worn by a batter, which may include, but is not limited to: one or more ankle guards 1320; a helmet 1325; and one or more elbow guards. Finally, FIG. 13C illustrates such protective equipment worn by a pitcher, which may include, but is not limited to, a face mask 1340 and a heart guard 1335. Any, or all, of the pads included in these protective pieces may be and/or may include a moldable portion that is comprised of a mixture of the polymer blend described herein.

Figure 14:
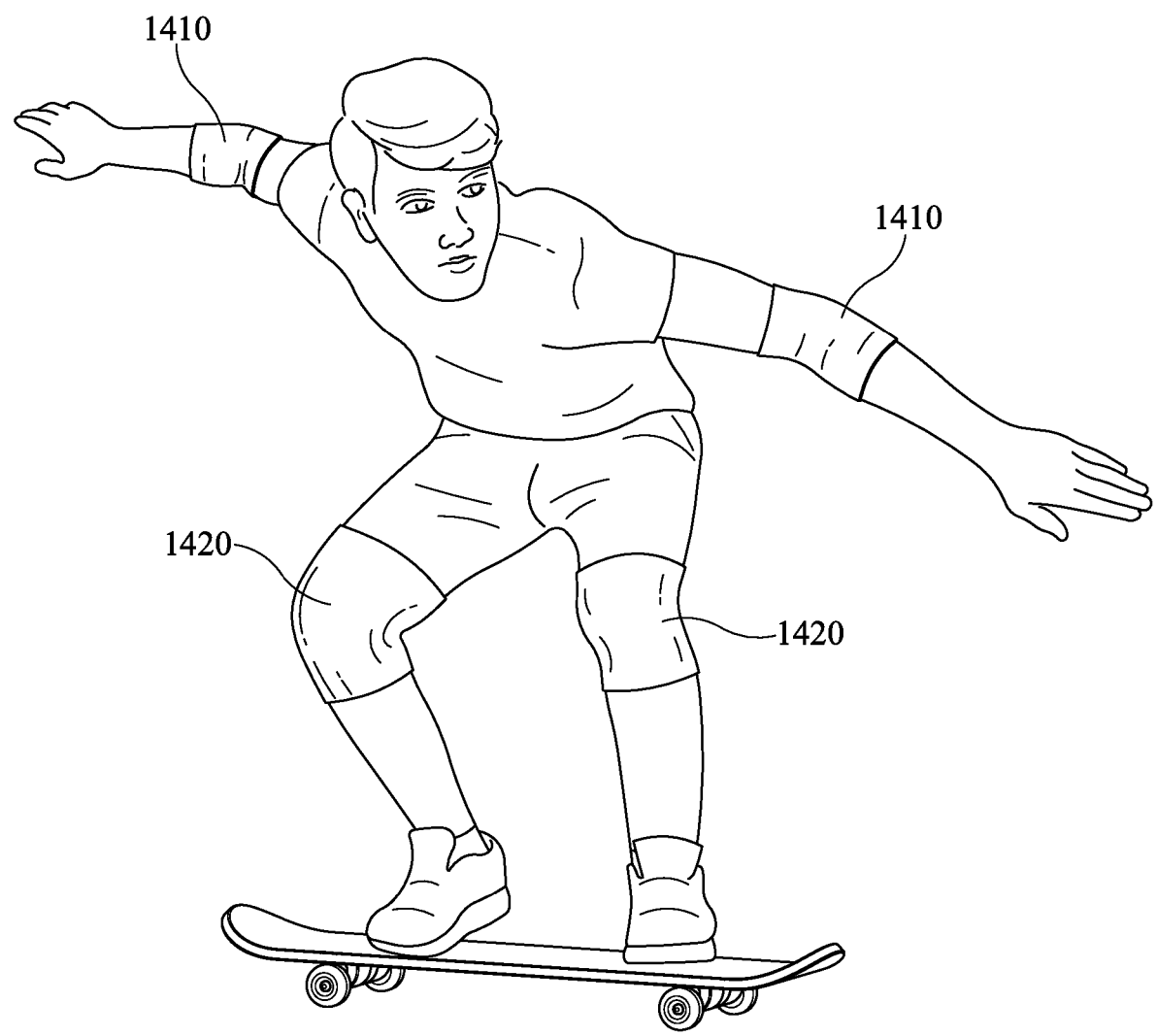
FIG. 14 illustrates a perspective view of exemplary elbow and knee guards on a skateboarder consistent with some embodiments of the invention.

FIG. 14 illustrates a non-limiting example of some various types of protective equipment typically utilized by skateboarders. Such equipment may include, but is not limited to, elbow pads 1410 and knee pads 1420. The pads included in these protective pieces may be and/or may include a moldable portion that is comprised of a mixture of the polymer blend described herein.

Figure 15:
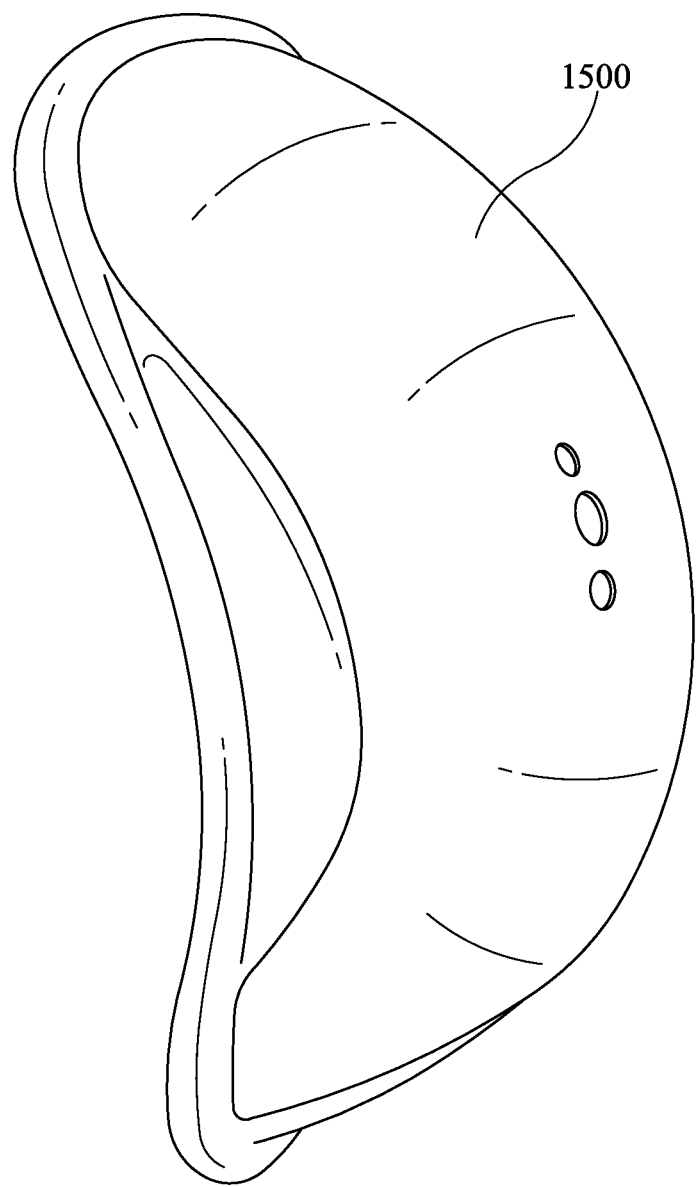
FIG. 15 illustrates a perspective view of an exemplary athletic cup consistent with some embodiments of the invention.

Additionally, protective cups or athletic cups may be worn in many sports, including but not limited to, hockey, football, baseball, rugby, lacrosse, soccer, mixed martial arts, or other contact sports. FIG. 15 illustrates an exemplary athletic cup 1500 that may include a moldable portion that is comprised of a mixture of the polymer blend described herein. In some instances, the exterior-facing portion of the athletic cup 1500 may be constructed of one or more grades of Vistamaxx™ and be moldable to the user's anatomy as described herein. In other instances, the interior-facing portion of the athletic cup 1500 (the portion that contacts the user) may be constructed of one or more grades of Vistamaxx™ and be moldable to the user's anatomy as described herein, In still other instances, both the exterior-facing and interior-facing portions of the athletic cup may be constructed of moldable portions as described herein.

Figure 16:
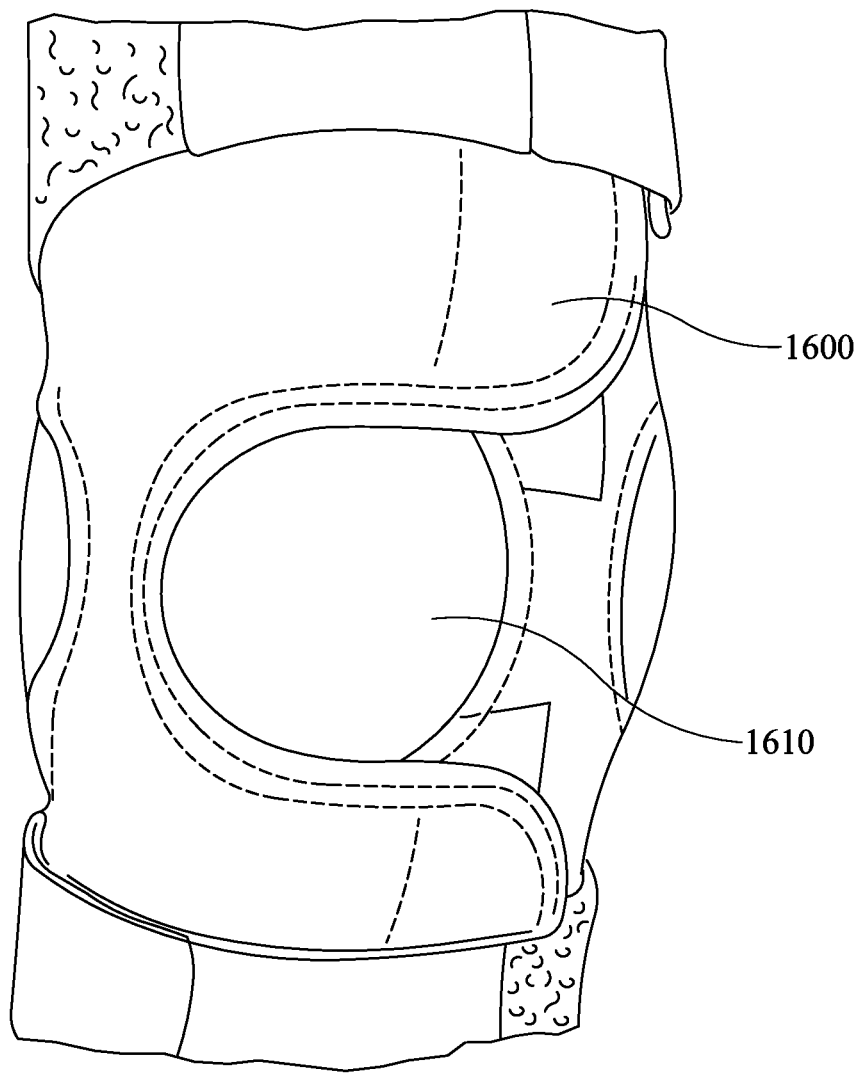
FIG. 16 illustrates a perspective view of an exemplary knee brace consistent with some embodiments of the invention.

FIG. 16 illustrates a non-limiting example of a knee brace 1600 that, in some instances may be worn when the knee is injured. The knee brace 1600 may include be, or may include, a moldable portion comprised of a mixture of the polymer blend described herein. In some instances, particularly where partial movement of the knee is desired, the knee brace 1600 may additionally include a cutout 1610 at the joint. Such a cutout may allow for movement, while also supporting the knee. In other instances, the knee brace may be a brand that is positioned either directly above or directly below the joint, for example as used to treat iliotibial band syndrome.

Figure 17:
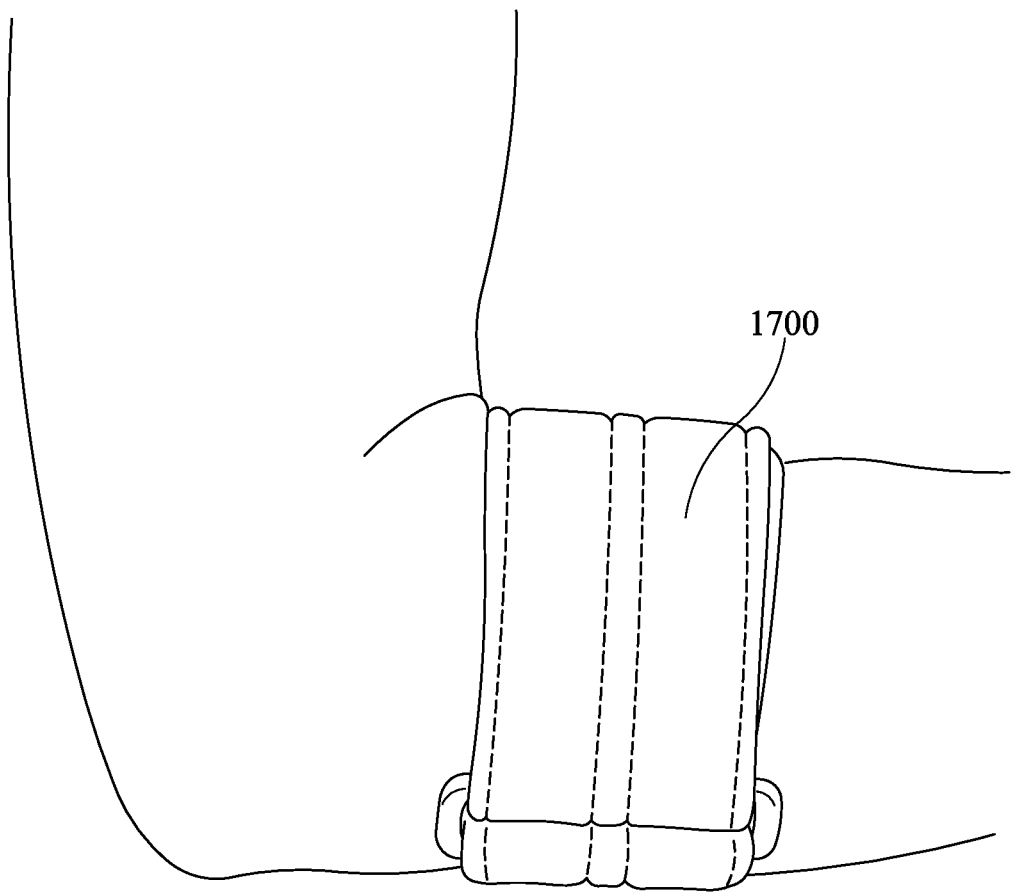
FIG. 17 illustrates a perspective view of an exemplary elbow brace consistent with some embodiments of the invention.

FIG. 17 illustrates a non-limiting example of an elbow brace 1700 that, in some instances may be worn when the elbow is injured, for example, when a user's has tennis elbow. The elbow brace 1700 may include be, or may include, a moldable portion comprised of a mixture of the polymer blend described herein. Similar to the guard illustrated in FIGS. 1A-C, the elbow brace 1700 may include an outer layer and a moldable inner layer. For example, the outer layer may be a cover that is configured to couple with the moldable inner layer, and may be constructed of a soft, fabric material, such as a moisture wicking fabric (e.g. polyester, nylon, rayon, blends, neoprene, or the like). In some instances, the moldable inner layer of the elbow brace 1700 may be in direct contact with the user (similar to the embodiment illustrated in FIG. 1B); while in other instances, the outer layer of the elbow brace 1700 may form a sleeve configured to envelop the inner moldable layer (similar to the embodiment illustrated in FIG. 1C).

EXAMPLES

Example 1

In a first example, the composition of the moldable portion may range between 85%-99% wt. Vistamaxx™ 3000 and between 1% and 15% wt. microwave susceptor. More particularly, the composition of the moldable portion may be 95% wt. Vistamaxx™ 3000 and 5% wt. microwave susceptor. Still even more particularly, the composition of the moldable portion may be 95% wt. Vistamaxx™ 3000 and 5% wt. carbon black. The resulting moldable portion may be, or be used as a part of, a guard or piece of protective equipment to be worn by a user. The resulting moldable portion may be softer than typically plastic guards while also having increased impact absorption capabilities as compared to typically plastic guards. A moldable portion according to Example 1 may be heated utilizing dry heating means (e.g. by heating in a microwave oven for 1 to 2 minutes). Furthermore, the moldable portion according to Example 1, has a slower rate of crystallization compared to traditionally moldable parts (e.g. ethylene vinyl acetate (EVA)), thus allowing for a longer fitting period, which increases the likelihood a user obtains a proper fit to their particular anatomy. Table 2 lists various properties of a moldable portion according to Example 1 as compared to a composition of EVA (28% vinyl acetate).

TABLE 2

| Physical and Mechanical Property | Example 1 | EVA (28% vinyl acetate) |
|---|---|---|
| Density g/cc | 0.873 | 0.95 |
| Tensile Strength at 100% (psi) | 679 | N/A |
| Tensile Strength at 300% (psi) | 701 | N/A |
| Tensile Strength at Break (psi) | >2000 | 2800 |
| Die C Tear Strength (ibf/in) | 365 | 250 |
| Flexural Modulus 1% secant (psi) | 9050 | 2300 |
| Hardness (Shore A/D) | 27D | 80A |
| Vicat Softening Temperature (° C.) | 65.1 | 48.9 |
| Temperature Required to Become Pliable (° C.) | 60-100 | 70 |
| Fitting Time before Composition Hardens | 2-3 minutes | 10-20 seconds |

Example 2

In a second example, the composition of the moldable portion may include two or more grades of Vistamaxx™ blended at varying percentages in order to achieve a desired level of hardness. Vistamaxx™ 3980L and Vistamaxx™ 6102 may be combined to achieve a desired hardness and impact resistance. According to this example, the composition of the moldable portion may range between 0-99% wt. Vistamaxx™ 3980L, between 0-99% Vistamaxx™ 6102, and between 1% and 15% wt. microwave susceptor. More particularly, the moldable portion composition according to Example 2 may include 5% wt. carbon black as the microwave susceptor. Such a blend of Vistamaxx™ 3980L and Vistamaxx™ 6102 allows for compositions of moldable portions with varied hardness and impact resistance properties. This variability allows a moldable portion of a guard to be targeted to the specific type of guard. For example, a shin guard utilized by a soccer player may require a harder composition compared to ankle or wrist guard. A moldable portion according to Example 2 may be heated utilizing dry heating means (e.g. microwave oven). Furthermore, the moldable portion according to Example 2, has a slower rate of crystallization compared to traditionally moldable parts (e.g. ethylene vinyl acetate (EVA)), thus allowing for a longer fitting period, which increases the likelihood a user obtains a proper fit to their particular anatomy. Table 3 lists various properties of a moldable portion according to Example 2 as compared to a composition of EVA (28% vinyl acetate).

TABLE 3

| Physical and Mechanical Property | Example 2 | EVA (28% vinyl acetate) |
|---|---|---|
| Density g/cc | 0.86-0.88 | 0.95 |
| Tensile Strength at 100% (psi) | 324-953 | N/A |
| Tensile Strength at 300% (psi) | 402-1030 | N/A |
| Tensile Strength at Break (psi) | 1100-2800+ | 2800 |
| Die C Tear Strength (ibf/in) | 190-476 | 250 |
| Flexural Modulus 1% secant (psi) | 2090-17000 | 2300 |
| Hardness (Shore A/D) | 67A-34D | 80A |
| Vicat Softening Temperature (° C.) | 53.9-77.3 | 48.9 |
| Temperature Required to Become Pliable (° C.) | 60-100 | 70 |
| Fitting Time before Composition Hardens | 2-3 | 10-20 seconds |

Example 3

A moldable portion of a guard or piece of protective equipment is formed by any polymer according to Examples 1 or 2 in further combination with a foaming agent. In particular, with the foaming agent Ecocell® produced by Polyfil, Rockaway, N.J. 07866. A moldable portion according to Example 3 may be heated utilizing dry heating means (e.g. microwave oven). Furthermore, the moldable portion according to Example 3, has a slower rate of crystallization compared to traditionally moldable parts (e.g. ethylene vinyl acetate), thus allowing for a longer fitting period, which increases the likelihood a user obtains a proper fit to their particular anatomy.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of," or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A moldable portion configured to be used as at least a part of a guard, comprising:

a thermoplastic semi-crystalline propylene ethylene copolymer having a crystallinity of about 2% to about 65% comprising between about 85% to about 99% of the moldable portion, wherein the thermoplastic semi-crystalline propylene ethylene copolymer is a chiral metallocene catalyzed copolymer of propylene and ethylene;

a microwave susceptor comprising about 1% to about 15% of the moldable portion; and wherein the moldable portion is prepared for customization by heating to a temperature of 60° C. to 100° C., thereby forming a pliable moldable portion wherein the pliable moldable portion is placed directly on an area of a user's anatomy and customized to the user's anatomy.

2. The moldable portion of claim 1, wherein the moldable portion is coupled with an outer layer to form the guard.

3. The moldable portion of claim 1, wherein the moldable portion is enveloped by a sleeve to form the guard.

4. The moldable portion of claim 1, wherein the thermoplastic semi-crystalline propylene ethylene copolymer has an ethylene content of 11% by weight, wherein the thermoplastic semi-crystalline propylene ethylene copolymer has a viva softening point of 65° C., and the thermoplastic semi-crystalline propylene ethylene copolymer has a flexural modulus of 9050 psi.

5. The moldable portion of claim 1, wherein the thermoplastic semi-crystalline propylene ethylene copolymer is a blend including between about 1% and about 99% of a first copolymer and between about 1% to about 99% of a second copolymer, wherein the first copolymer has an ethylene content of 9% by weight, a viva softening point of 77.3° C., and a flexural modulus of 17000 psi; and wherein the second copolymer has an ethylene content of 16% by weight, a viva softening point of 53° C., and a flexural modulus of 2090 psi.

6. The moldable portion of claim 1, wherein the microwave susceptor is carbon black.

7. The moldable portion of claim 1 further comprising a foaming agent configured to generate air spaces in the thermoplastic semi-crystalline propylene ethylene copolymer.

8. The moldable portion of claim 1, wherein the moldable portion remains moldable for about 2 to 3 minutes as the temperature falls below 60° C. following heating.

9. The moldable portion of claim 1, wherein the moldable portion is adapted to be reformed to an area of the user's anatomy it is intended to protect by reheating to a temperature of about 60° C. to about 100° C.

10. A customizable guard, comprising:
a moldable portion, wherein the moldable portion comprises:
    a thermoplastic semi-crystalline propylene ethylene copolymer having a crystallinity of about 2% to about 65% comprising between about 85% to about 99% of the moldable portion, wherein the thermoplastic semi-crystalline propylene ethylene copolymer is a chiral metallocene catalyzed copolymer of propylene and ethylene, and
    a microwave susceptor comprising about 1% to about 15% of the moldable portion;
    wherein the moldable portion is placed directly on an area of a user's anatomy and customized to the user's anatomy it is intended to protect, and
    wherein the moldable portion is prepared for customization by heating to a temperature of 60° C. to 100° C.; and
an outer layer coupled with the moldable portion.

11. The customizable guard of claim 10, wherein the outer layer is removably coupled with the moldable portion, wherein the moldable portion is further prepared for customization by decoupling from the outer layer.

12. The customizable guard of claim 10, wherein the outer layer is a sleeve configured to envelop the moldable portion.

13. The customizable guard of claim 12, wherein the sleeve includes a first exterior surface configured to contact the user and a second exterior surface configured to face outward relative to the user, wherein the moldable portion is disposed within a first exterior layer and second exterior layer.

14. The customizable guard of claim 10, wherein the thermoplastic semi-crystalline propylene ethylene copolymer has an ethylene content of 11% by weight, wherein the thermoplastic semi-crystalline propylene ethylene copolymer has a viva softening point of 65° C., and the thermoplastic semi-crystalline propylene ethylene copolymer has a flexural modulus of 9050 psi.

15. The customizable guard of claim 10, wherein the thermoplastic semi-crystalline propylene ethylene copolymer is a blend including between about 1% and about 99% % of a first copolymer and between about 1% to about 99% of a second copolymer, wherein the first copolymer has an ethylene content of 9% by weight, a viva softening point of 77.3° C., and a flexural modulus of 17000 psi; and wherein the second copolymer has an ethylene content of 16% by weight, a viva softening point of 53° C., and a flexural modulus of 2090 psi.

16. The customizable guard of claim 10, wherein the microwave susceptor is carbon black.

17. The customizable guard of claim 10, wherein the moldable portion further comprises a foaming agent configured to generate air spaces in the thermoplastic semi-crystalline propylene ethylene copolymer.

18. The customizable guard of claim 10, wherein the moldable portion is adapted to be reformed to an area of the user's anatomy it is intended to protect by reheating to a temperature of about 60° C. to about 100° C.

19. A method of customizing a guard to a user's individual anatomy, the method including:
obtaining a moldable portion, wherein the moldable portion includes:
    a thermoplastic semi-crystalline propylene ethylene copolymer having a crystallinity of about 2% to about 65% comprising between about 85% to about 99% of the moldable portion, wherein the thermoplastic semi-crystalline propylene ethylene copolymer is a chiral metallocene catalyzed copolymer of propylene and ethylene, and
    a microwave susceptor comprising about 1% to about 15% of the moldable portion;
dry heating the moldable portion to a temperature of 60° C. to 100° C.;
applying the moldable portion to an anatomical region of the user; and
setting the moldable portion, thereby forming a set moldable portion.

20. The method of customizing a guard to a user's individual anatomy of claim 19 further comprising:

reheating, by dry heating, the set moldable portion a temperature of 60° C. to 100° C., thereby forming a reformable moldable portion;

applying the reformable moldable portion to an anatomical region of the user; and setting the reformable moldable portion.

* * * * *